(12) United States Patent
Van Den Ende et al.

(10) Patent No.: US 10,830,218 B2
(45) Date of Patent: Nov. 10, 2020

(54) ACUPRESSURE DEVICE

(71) Applicant: KONINKLIJKE PHILIPS N.V., Eindhoven (NL)

(72) Inventors: Daan Anton Van Den Ende, Breda (NL); Sander Theodoor Pastoor, Vleuten (NL); Yanchun Zhang, Vught (NL); Kars-Michiel Hubert Lenssen, Veldhoven (NL); Warner Rudolph Theophile Ten Kate, Waalre (NL); Alex Ivanov, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 288 days.

(21) Appl. No.: 15/759,557

(22) PCT Filed: Sep. 13, 2016

(86) PCT No.: PCT/EP2016/071568
§ 371 (c)(1),
(2) Date: Mar. 13, 2018

(87) PCT Pub. No.: WO2017/046089
PCT Pub. Date: Mar. 23, 2017

(65) Prior Publication Data
US 2019/0151193 A1    May 23, 2019

(30) Foreign Application Priority Data

Sep. 16, 2015 (EP) .................................. 15185504

(51) Int. Cl.
*F03G 7/06* (2006.01)
*A61H 39/04* (2006.01)
*A61N 1/36* (2006.01)

(52) U.S. Cl.
CPC .............. *F03G 7/06* (2013.01); *A61H 39/04* (2013.01); *A61H 2201/0228* (2013.01);
(Continued)

(58) Field of Classification Search
CPC ............ A61H 39/04; A61H 2201/1207; A61H 2201/165; A61H 2230/655; A61H 2201/0228; F03G 7/06; A61N 1/36014
See application file for complete search history.

(56) References Cited

U.S. PATENT DOCUMENTS 4,411,258 A * 10/1983 Pujals, Jr. .............. A61H 39/04
                                                           601/134
5,607,749 A *  3/1997 Strumor ................. A43B 7/146
                                                           428/156
(Continued)

FOREIGN PATENT DOCUMENTS

CN    1092971 A    10/1994
CN    2885238 Y    4/2007
(Continued)

OTHER PUBLICATIONS

Yeung, Wing-Fai et al., "Acupressure, reflexology, and auricular acupressure for insomnia: A systematic review of randomized controlled trials", Sleep Medicine, vol. 13, issue 8, pp. 971-984, 2012.
(Continued)

*Primary Examiner* — Phong Son H Dang

(57) ABSTRACT

The invention provides a health device for automatically administering skin pressure-based therapies to a user. The device comprises one or more actuator members, each comprising a smart shape-changing material of a class which is disposed to change shape in response to a change in temperature or to the application of an electrical stimulus.

(Continued)

The actuator members are controlled by a controller to apply pressure to one or more points on a user's skin.

11 Claims, 5 Drawing Sheets

(52) U.S. Cl.
CPC .............. *A61H 2201/1207* (2013.01); *A61H 2201/165* (2013.01); *A61H 2230/655* (2013.01); *A61N 1/36014* (2013.01)

(56) References Cited

U.S. PATENT DOCUMENTS

| | | | | |
|---|---|---|---|---|
| 5,774,424 | A * | 6/1998 | Yoo | A61H 7/001 368/10 |
| 5,997,465 | A * | 12/1999 | Savage | A62B 17/008 600/20 |
| 6,113,620 | A * | 9/2000 | Chung | A61H 39/04 606/189 |
| 6,228,103 | B1 * | 5/2001 | Grey | A61H 39/04 601/107 |
| 6,305,040 | B1 * | 10/2001 | Myler | A61H 39/04 5/630 |
| 6,361,550 | B2 * | 3/2002 | Grey | A61H 39/04 601/107 |
| 7,637,883 | B2 * | 12/2009 | Nyi | A61F 5/30 602/20 |
| D639,971 | S * | 6/2011 | Schwartz | D24/200 |
| 2009/0013684 | A1 * | 1/2009 | Takahashi | F03G 7/065 60/527 |
| 2010/0234779 | A1 | 9/2010 | Asvadi et al. | |
| 2013/0064627 | A1 * | 3/2013 | Beeler | F03G 7/06 413/1 |
| 2018/0242655 | A1 * | 8/2018 | Holschuh | A41D 1/005 |

FOREIGN PATENT DOCUMENTS

| | | |
|---|---|---|
| CN | 102100633 A | 6/2011 |
| JP | H06327745 A | 11/1994 |
| JP | 2004305581 A | 11/2004 |
| JP | 2005334290 A | 12/2005 |
| JP | 2009172032 A | 8/2009 |
| JP | 2012196405 A | 10/2012 |
| JP | 2013073465 A | 4/2013 |

OTHER PUBLICATIONS

Bray, Patricia A. et al., "Modulation of the Sleep State-Dependent P50 Midlatency Auditory-Evoked Potential by Electric Stimulation of Acupuncture Points", Archives of Physical Medicine and Rehabilitation, vol. 86, issue 10, pp. 2018-2026, 2005.

Mayer-Gindner, A. et al., "Newly Explored Electrical Properties of Normal Skin and Special Skin Sites", Biomedical Engineering, vol. 49, issue 5, pp. 117-124, 2004.

Ahn, A. et al., "Electrical impedance along connective tissue planes associated with acupuncture meridians", BMC Complementary and Alternative Medicine, 2005.

Reichmanis, M. et al., "Electrical correlates of acupuncture points", IEEE transactions on bio-medical engineering, vol. 22, issue 6, pp. 533-535, Nov. 1975.

Hong, M. et al., "Heterogeneity of Skin Surface Oxygen Level of Wrist in Relation to Acupuncture Point", Evidence-Based Complementary and Alternative Medicine, 2012.

2004 Annual Index—IEEE Engineering in Medicine and Biology Magazine—vol. 23, Engineering in Medicine and Biology Magazine, IEEE (vol. 24 issue 1 pp. 110,111,112,113,114,115,116,117,118,119 ), Jan. 2005.

Feng, I. et al., "Further study on the anatomical, histological and biochemical bases underlying clinical acupuncture effectiveness", J Chin Med, 15(2): 69-78, 2004.

* cited by examiner

ACUPRESSURE DEVICE

CROSS-REFERENCE TO PRIOR APPLICATIONS

This application is the U.S. National Phase application under 35 U.S.C. § 371 of International Application Serial No. PCT/EP2016/071568, filed on 13 Sep. 2016, which claims the benefit of European Application Serial No. 15185504.6, filed on 16 Sep. 2015. These applications are hereby incorporated by reference herein.

FIELD OF THE INVENTION

This invention relates to a device for administering pressure-based therapies to a user, and method for the same.

BACKGROUND OF THE INVENTION

Insomnia is a sleep disorder affecting an increasingly large number of people across the modern world. Some surveys have reported that up to 30% of people may experience regular symptoms of insomnia, with 10% suffering significant symptoms causing them problems of fatigue during their waking hours. It is reported that up to 10% may have chronic insomnia.

Insomnia is a particularly significant problem in China. A recent study has suggested that prevalence of insomnia in China may be as high as 40%, higher than the global average.

One traditional healing therapy which is still used widely today in treating insomnia—as well as a whole range of other conditions—is Acupressure. Acupressure and acupuncture originate in China and Asia, and, although the therapy is today to be found employed in a wide range of different countries of the world, its usage remains most prevalent in its originating homelands.

Acupressure involves the application of localised pressure to regions of the body, triggering release of muscle tension, lowering of blood pressure and providing stimulation to deeper skin tissue. It also helps to increase blood flow locally, triggers the release of endorphins (natural painkillers and mood elevators) and suppresses the release of certain stress hormones.

Acupressure employs the application of pressure to areas of the skin which are known to be particularly sensitive to bioelectrical impulses. In traditional Chinese medicine, stimulation of these points is thought to enhance the flow of human energy. Several points, such as the P6 point on the wrist, B138 between the shoulder blades, B110, GB20 and GV16 on the back of the neck, CV17 on the chest and also the KD1 point on the sole of the foot (popularly dubbed the "sleep point") are known to stimulate healthy sleep. The application of pressure is often done manually by a trained professional.

Acupressure points are known to coincide with so-called Bio Active Points (BAPs), these being points on the human body where nerve-fiber bundles penetrate the hypodermis and dermis of the skin. These nerve endings are very small, and the density of never fiber bundles at BAPs is locally very high, which causes the skin to exhibit a very low electrical resistance in the vicinity of these points. In addition, in some cases, BAPs are closely related to acupuncture points, with around 80% of all known acupuncture points exhibiting similar anatomical skin structures to BAPs.

Bioactive points (or Acupoints) differ anatomically, histologically and biochemically to surrounding tissue. In particular, Acupoints display larger concentrations of mucopolysaccharides, collagen fibers and nerve endings than surrounding tissue. Acupoints and meridians have also been shown to exhibit lower electrical resistance and higher capacitance than surrounding cutaneous areas. There has also been shown to be higher oxygen content in the vicinity of Acupoints.

Certain correlations are also known to exist between Acupoints and brain activity. Studies have shown, for example, that local stimulation of Acupoints triggers the activation of a specific associated region of the brain.

Many studies have demonstrated the effectiveness of acupressure treatment on sleep disorders.

One review paper (Wing-Fai Yeung, et al. *Acupressure, reflexology, and auricular acupressure for insomnia: A systematic review of randomized controlled trials*) has presented a systematic review of acupressure-based treatments for insomnia. It reports that acupressure was significantly more effective than placebo acupressure in all 6 studies in which such a comparison was undertaken. Pooled analysis of three moderate-quality studies also identified a significant improvement in the results of subjective sleep questionnaire scores—namely PSQI and AIS.

Another paper (Bray, P., Garcia-Rill, E., et al "*Modulation of the Sleep State—Dependent P50 Midlatency Auditory-Evoked Potential by Electric Stimulation of Acupuncture Points*") has described the effects of electrical stimulation of acupoints in relation to sleep quality. The paper presents a study which was designed to systematically test stimulation of specific acupoints known to be related to arousal, and investigate their potential for modulating the sleep-state dependent P50 potential.

Electroacupuncture at specific points (PC6, HT3, LR3) decreased P50 potential amplitude. From this it may be concluded that this therapy may be effectively used to decrease arousal levels. The results suggest that surface stimulation of specific acupuncture points modulates the manifestation of the sleep-state dependent P50 potential, so long as certain parameters of stimulation are used.

The effects of electroacupuncture were found to begin during the period of stimulation and to outlast the stimulation episode. Moreover, repeated episodes of stimulation were found to be additive in decreasing P50 potential amplitude. This implies a direct effect on arousal level, making electroacupuncture a potential therapy for conditions in which hypervigilance is a symptom. Such disorders include schizophrenia, depression, and anxiety disorders. Insomniacs too exhibit hyperarousal characteristics, making this therapy highly suitable for treatment of insomnia.

The P50 mid-latency auditory-evoked potential is a sleep-state dependent waveform. It has three primary characteristics: (1) it is present during synchronization of fast cortical rhythms such as waking a rapid eye movement (REM) sleep but absent during synchronization of slow rhythms as in deep slow-wave sleep (i.e. it is state-dependent); (2) it is blocked by the cholinergic antagonist acopolamine (i.e. it is mediated by cholinergic neurons); and (3) it habituates rapidly at stimulation rates greater than 2 Hz.

To administer acupressure effectively, a high degree of skill and precision is required. The area to which pressure is applied must be precisely located, the magnitude of pressure applied must be carefully controlled, and the duration and pattern of applied pressure must be appropriate for the condition being treated. For this reason, a trained professional is often employed to administer the therapy. Alternatively, there also exist many books and training courses which offer tuition on self-acupressure therapy.

However, both of these options carry disadvantages both in terms of convenience and cost. It is not always practical or affordable to visit a trained therapist—especially where repeated sessions are required. Undergoing self-training too may prove impractical or unduly burdensome for most people.

Moreover, when it comes in particular to therapy for treating insomnia, where the therapy is required to be administered during the onset and throughout the course of a person's natural sleep cycle, the external manual administering of the therapy by either the patient themselves or a $3^{rd}$ party professional is completely impracticable.

There is a need therefore for a means of administering acupressure-based therapies automatically to a patient without the need for either the patient or a third party to be actively involved.

Certain devices do exist which claim to provide such functionality. In particular, in very common usage are a number of wristband-based devices, which use an attached solid tag element to apply to a point on the wrist of a user a constant pressure for the duration of the time that the device is worn.

However, these devices are capable only of delivering pressures of a fixed, unmodulated magnitude, which is known to be unsatisfactory in providing true, effective acupressure therapy.

Required is a device capable of automatically delivering pressures of a variable magnitude, which can hence be modulated over time in accordance with a particular pattern known to be effective in delivering true acupressure therapy.

U.S. Pat. No. 6,228,103 B1 discloses one device which attempts such a solution, in which a motorised cam member is incorporated into a wearable strap and adapted to rotate to provide a cyclically varying pressure over time.

However, in all embodiments of this device, the modulating pressure is provided by means of a mechatronic motor element. Such elements however—as the state of the art currently stands—necessarily have a significant form factor, and incur substantial added bulk and weight to the device, making them far from ideal for the purposes of incorporation within a device intended to be worn comfortably and unobtrusively by a user. They are in particular highly undesirable for use in treating insomnia, where the bulky/heavy nature of the device, as well as the (comparatively) large moving parts will tend to disrupt or disturb natural sleep, and prevent comfortable use of the device on any part of the body to which the user must apply their weight (i.e. lay on) during the course of sleep.

There is a requirement therefore for a device capable of automatically delivering variable pressures to one or more acupoints of a user's body over a time, but wherein the means of delivering said variable pressures has a thinner, more compact and less obtrusive form factor, improving the comfort of the device when worn by a user—in particular to the extent that the device may be worn and operated comfortably during sleep without disturbing or interrupting natural sleep cycles.

SUMMARY OF THE INVENTION

The invention is defined by the claims.

According to an aspect of the invention, there is provided a health device for applying pressure to one or more areas of a user's skin, comprising:

one or more actuator members, each comprising a smart shape-changing material of a class which is disposed to change shape in response to a change in temperature or to the application of an electrical stimulus;

one or more stimulating means to deliver thermal or electrical stimuli to the one or more actuator members, for stimulating shape change of the smart shape-changing material; and a controller adapted to control the one or more stimulating means in order to stimulate the shape-changing materials of the one or more actuator members to deliver pressures to one or more pressure delivery areas of a user's skin.

The one or more stimulating means comprise electrodes, operatively coupled with the controller and electrically coupled to the smart shape-changing material of each actuator member, and adapted to deliver electrical stimuli generated by the controller to the smart shape-changing material.

Furthermore, the device also comprises one or more skin stimulation elements, electrically connected with the controller, for transferring electrical stimuli to one or more areas of a user's skin. The electrical stimuli transferred by the one or more skin stimulation elements are generated by the controller and are for sensing an impedance of the skin, wherein the controller is adapted to determine an impedance of the skin through measuring one or more electrical parameters of the delivered electrical stimuli.

Smart shape changing materials are characterised in being able to deliver large actuation forces with a very small active component, in response to the application of an external stimulus, such as a temperature change or the application of an electric field or current. A profile of less than 1 mm, for example, is achievable with these materials. Embodiments of the invention are based on the utilisation of strips, layers or other elements of smart shape-changing material to provide highly compact actuator members capable of delivering substantial actuation force which may be harnessed to provide automated skin pressure-based therapies to a user.

This is in contrast for example to mechatronic actuation based devices (comprising motors for instance) which are typically bulky and obtrusive and consequently uncomfortable for a user to wear. They are in particular unsuitable for use in treating insomnia, where the bulky and heavy nature of the device, as well as the (comparatively) large moving parts, tend to disrupt or disturb sleep. The thin form factor of smart material actuators furthermore allows use of embodiments of the invention on parts of the body on which the user may naturally tend to lay or apply their weight during sleep, without causing discomfort.

Smart shape changing materials may include, by way of non-limiting example, shape memory alloy materials—which are disposed to deform in response to thermal stimulation—and electroactive polymer materials—which are disposed to deform in response to electrical stimulation. Other smart shape changing materials include shape-memory polymers, which deform in response to thermal stimuli.

As discussed above, acupoints (or Bioactive Points) are characterised by the presence of a locally large density of nerve endings (nerve fibre bundles) which cause these areas to exhibit a very low electrical resistance. Hence, impedance sensing allows for the detection of acupoints locations on user's skin through looking for local minima of impedance.

The controller may be adapted to control the one or more stimulating means such that the shape-changing materials of the actuator members are stimulated to deliver pressures which vary in magnitude over time. In particular, the magnitudes over time may be controlled in examples so as to administer from the device an acupressure therapy.

The varying of the magnitudes may in simple examples comprise a binary variation between zero magnitude and a fixed non-zero magnitude—i.e. the varying may comprises simply a switching on and switching off of a fixed magnitude applied pressure. In other examples, the actuator member may be stimulable to apply a spectrum or discrete range of pressure magnitudes.

As discussed above, true acupressure therapy requires the application of variant pressure over the course of the therapy. The application of constant pressure to an acupoint for an extended period does not achieve good results; rather the pressure must intermittently be released and reapplied, or at least diminished and then increased periodically. Embodiments of the invention allow for this functionality to be provided.

In particular examples, the varying of the magnitudes over time may be controlled so as to administer from the device an acupressure therapy for the treatment of insomnia.

The health device may be a wearable health device comprising a securing means for holding the one or more actuator members against the one or more pressure delivery areas of a user's skin. The securing means may comprise for example one or more adhesive patches or strips.

According to one set of embodiments, the smart shape-changing material may be a shape memory alloy material, disposed to change between a first shape and a second shape in response to a change in temperature from below to above a particular phase-transition temperature, and Shape memory alloys (SMAs) are capable of producing several hundred MPa stresses and large deformation, making them very powerful actuator solutions with only a very small form factor. In particular, a typical SMA may be able to apply 2-10N of out of plane force per 1×1 mm$^2$ cross section strip of material of 10 cm length (force depends on displacement amplitude).

The smart shape-changing material may be a shape memory alloy material, disposed to change between a first shape and a second shape in response to a change in temperature from below to above a particular phase transition temperature, and wherein the controller is adapted to deliver currents to the electrodes coupled to the shape memory alloy materials of each actuator member in order to stimulate Joule heating of said shape memory alloy materials.

In these cases, the one or more skin stimulation elements may be formed by one or more area portions of the shape memory alloy materials. Here, embodiments of the device are able to provide combined actuation and impedance sensing (for acupoint identification) functionality by means of a single actuator member component. Where the actuator member comprises a shape memory alloy material, low level currents for impedance sensing may be transferred to the skin of a user directly via at least a portion of the (conductive) SMA. Not only does this simplify the device, it also means that impedance measurements may be acquired for regions of the skin which lay directly beneath pressure-applying areas of the actuator member(s) themselves (i.e. for pressure application points on the skin).

Hence embodiments conveniently allow impedance measurements to be taken, and actuation pressure applied, to the very same point on a user's skin, without the repositioning the device in-between. Detection of an acupoint (a point of low impedance) may be followed directly by application of pressure to that point, without further physical adjustment of the device.

In other examples, the smart shape-changing material may be an electroactive polymer material, disposed to change shape in response to the application of electrical stimuli, and wherein the controller is adapted to deliver voltages to the electrode for electrically stimulating the electroactive polymer material to change shape.

A typical EAP may be able to produce up to 2N for a single 12×12×0.3 mm$^3$ component.

In these cases, the one or more skin stimulation elements may be formed by one or more area portions of the electrodes coupled to the electroactive polymer materials of the actuator elements.

According to one or more of the above described embodiments, the controller may be operable to perform the steps of:

periodically or continually determining an impedance of the skin through measuring one or more electrical parameters of electrical stimuli delivered to the skin of a user by means of the one or more skin stimulation elements, thereby obtaining a set of skin impedance measurements;

analysing said determined impedance of the skin by comparing it with one or more reference values in order to determine whether said value corresponds to a minimum impedance point of the user's skin; and generating a sensory output by means of one or more sensory output elements, one or more parameters of the sensory output being dependent upon the result of said determination of whether or not the determined impedance corresponds to a minimum impedance point.

The reference values may correspond to one or more previously acquired impedance measurements, or may alternatively or additionally comprise one or more pre-determined threshold values. The reference values may in some cases correspond to determined values of one or more functions of one or more acquired values.

Examples of this embodiment allow for a user to be guided in appropriately positioning the device on their body such that the pressure-applying regions of the actuator members align with acupoints of their skin. The sensory output elements may comprise in examples one or more acoustic output elements such as speakers or buzzers or may comprise one or more optical output elements such as for example lighting elements (comprising e.g. LEDs or filament bulbs).

The user may for example—as part of an initial calibration/positioning exercise—sweep the device over a particular region of their skin, with impedance measures obtained continuously or periodically as they do so. Activation of the sensory output components allow the user to be alerted to the detection of a local impedance minimum (i.e. an acupoint)—and to the fact therefore that they should therefore hold the device at its present location and affix it to that point of their body.

In cases where the one or more actuator members comprise shape memory alloy materials, each of the one or more actuator members may—according to one set of examples—comprises a first shape memory alloy layer, a second shape memory alloy layer, and a thermal insulating layer disposed between the first and second shape memory alloy layers.

The two shape memory alloy layers may be provided in this case having differing 'memory shapes' (i.e. may be configured to deform into different shapes upon heating). In particular the first layer may be configured to deform in a first direction so as to apply an actuation pressure to the skin of a user, while the second may be configured to deform in the opposite direction, so as to allow 'resetting' of the first layer back to its original shape. The bi-layer structure hence provides intrinsic bi-directionality: the device may be actuated and reset without the requirement for any external biasing.

According to another set of examples, each of the one or more actuator members may instead comprise a first shape memory alloy layer and second shape memory alloy layer, the second being coupled to the first, and wherein the first and second layers have different phase transition temperatures.

Here, no thermal insulating layer is provided, but the two have different phase transition temperatures. The second layer allows for 'resetting' of the first layer according to similar principles as above, but is stimulated to deform, not by separate, isolated heating, but rather through raising the temperature of the whole actuator member system from below to above the phase transition temperature of the second layer.

Examples in accordance with another aspect of the invention provide a method of delivering pressure to one or more areas of a user's skin by means of a health device, the health device comprising one or more actuator members, each comprising a smart shape-changing material of a class which is disposed to change shape in response to a change in temperature or to the application of an electrical stimulus, and one or more stimulating means to deliver thermal or electrical stimuli to the one or more actuator members, for stimulating shape change of the smart shape-changing material;

the method comprising:

controlling the one or more stimulating means to stimulate the shape-changing materials of the one or more actuator members to deliver pressures to one or more pressure delivery areas of a user's skin.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a health device for automatically administering skin pressure-based therapies to a user, and a method for the same. The device comprises one or more actuator members, each comprising a smart shape changing material of a class which is disposed to change shape in response to a change in temperature or to the application of an electrical stimulus. The actuator members are controlled by a controller to apply pressure to one or more points on a user's skin.

The invention is based upon the incorporation of smart shape-changing material technology within an automated acupressure device, in order to provide a device capable of administering significant pressure to one or more points on a user's body in a time-varied fashion without incurring the large and bulky form factor of traditional mechatronic-based actuation components (such as electronic motors).

There are many varieties of smart shape-changing material, and their development has accelerated rapidly in recent decades, as an ever increasing range of advantageous applications for such materials has been discovered. The materials, in their broadest sense, are characterised in being materials whose shape or form may be deformed through the application of some external stimulus—such as heating or an electric field.

For the purposes of the present application, embodiments are outlined in detail which make use of two specific classes of smart shape-changing material in particular: Shape memory alloys (SMAs) and electroactive polymers (EAPs). Both materials are able to deliver force in the required acupressure force range. Typically a pressure of $30N/cm^2$ is needed over a pressure application regions of approximately $2.5 \times 2.5$ mm$^2$ for a well-positioned device (=1.9N force). The size of the whole device is of course larger than the spot size at which the acupressure is applied.

It should be understood however that the advantages conferred by the use of smart shape-changing materials is not limited to these two specific classes in particular, and that other classes may also be advantageously employed, such as, by way of non-limiting example, electro-active composites, electrostrictive ceramics or crystals, shape memory polymers, photomechanical materials, and/or magnetostrictive materials.

Shape memory materials (SMMs) are well known, in particular shape memory alloys (SMAs). The two main types of shape memory alloys are copper-aluminium-nickel, and nickel-titanium (NiTi), which is known as Nitinol. Nitinol is for example available in the form of a wire, rod and bar, or as a thin film. SMAs can however also be created by alloying zinc, copper, gold and iron.

SMAs can exist in two different phases, with three different crystal structures (twinned martensite, detwinned martensite and austenite). Nitinol alloys change from the martensite state to the austenite state when heated, and return when cooled.

Figure 1:
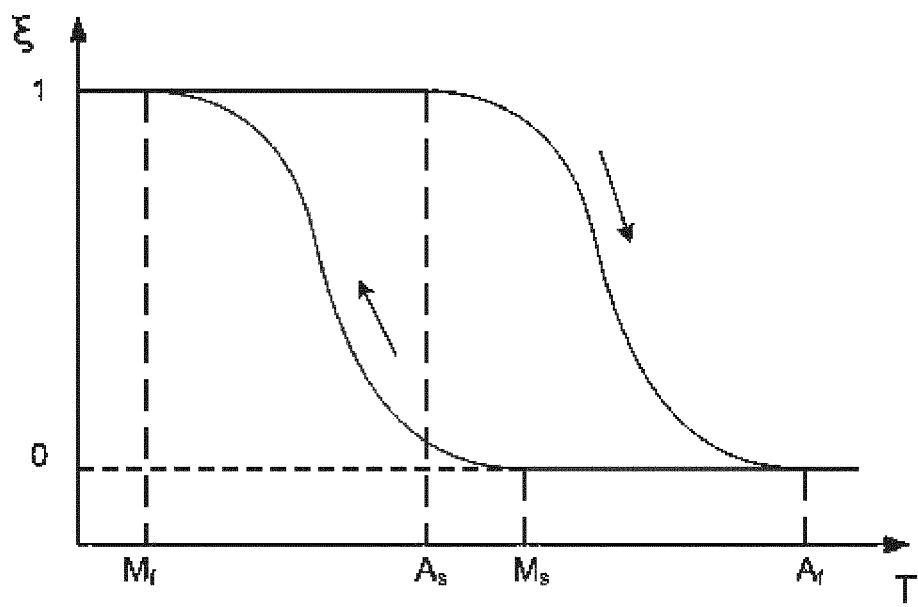
FIG. 1 shows the temperature-phase relationship for a shape memory alloy.

FIG. 1 shows the martensite fraction as a function of heating, during heating and cooling. During heating As and Af are the temperatures at which the transformation from martensite to austenite starts and finishes. The temperature As is the transition temperature. During cooling, Ms and Mf are the temperature at which the transition to martensite starts and completes.

The difference between the heating transition and the cooling transition gives rise to hysteresis where some of the mechanical energy is lost in the process. The shape of the curve depends on the material properties of the shape memory alloy, such as the alloying and work hardening.

The transition from the martensite phase to the austenite phase is only dependent on temperature and stress, not time. When a shape memory alloy is in its cold state (below As), the metal can be bent or stretched and will hold those shapes until heated above the transition temperature. Upon heating, the shape changes to its original shape. When the metal cools again it will change phase but not shape, and thus remain in the hot shape, until deformed again.

With this one-way effect, cooling from the high temperatures does not cause a macroscopic shape change. A deformation is necessary to recreate the low temperature shape. The transition temperature As for Nitinol is determined by the alloy type and composition and can vary from between −150° C. and 200° C. Generally, a transition temperature in the range −20° C. to 120° C. is used. Thus, the transition temperature can be tuned to a particular application.

There are also materials with a two way shape memory effect, based on cold work or hardening, with high stresses in the martensitic phase. However, the effect does not allow repeated temperature cycles, because stresses are released over time.

Figure 2:
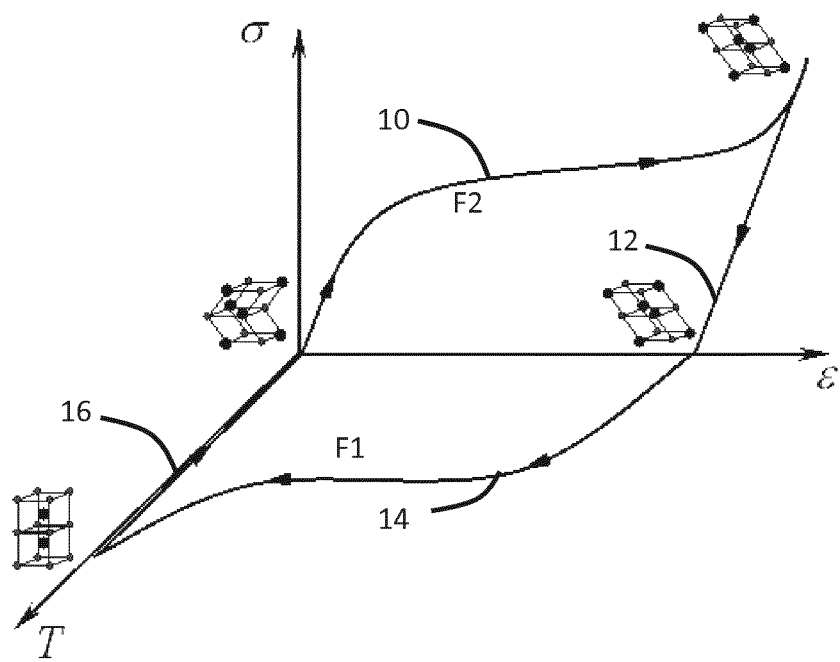
FIG. 2 shows the temperature—stress—strain relationship for a shape memory material.

As mentioned above, the phase transitions depend upon stress as well as temperature. FIG. 2 is a schematic diagram showing a stress-strain-temperature function for the shape memory effect. The stress is shown as σ and the strain is shown as ε.

The material is annealed to remember a specific shape. The material is deformed into its low temperature shape along path 10 by applying a stress to the material. This is a detwinning region. There is a sharp increase in slope in the stress-strain curve after which the material becomes much more difficult to deform further. Once the stress is relieved—shown as path 12—the large strain still stays in the material until heating above the transition temperature. This is the heating path 14 to bring the material to the austenite phase. It can then cool back into the twinned martensite phase along path 16 at which point the strain in the material has been relaxed (but the shape has not changed back).

The Modulus of Elasticity (E-modulus) of the high temperature phase of the SMA is significantly higher than the E-modulus of the low temperature phase.

The shape change that accompanies this phase change during heating is able to deliver a first force F1. After the temperature decrease below the phase change temperature, and thus after phase change to the low temperature phase, a lower force F2 is necessary to reshape the SMA into its original form (path 10 in FIG. 2).

Electro-active polymers are a group of polymers which exhibit a change in size or shape when stimulated by an electric field. In particular, electro-active polymers include electrostrictive polymers and ionic polymers, which are capable of generating a controlled deformation when a voltage is applied to them. The extent of deformation can be controlled by varying the applied voltage, which allows for a digital control over the displacement. In contrast to shape-memory alloys, wherein the high-temperature shape persists even after the material has re-entered the low temperature phase, an electro-active polymer reverts back to its original shape as soon as the electrical stimulus is removed.

Figure 3:
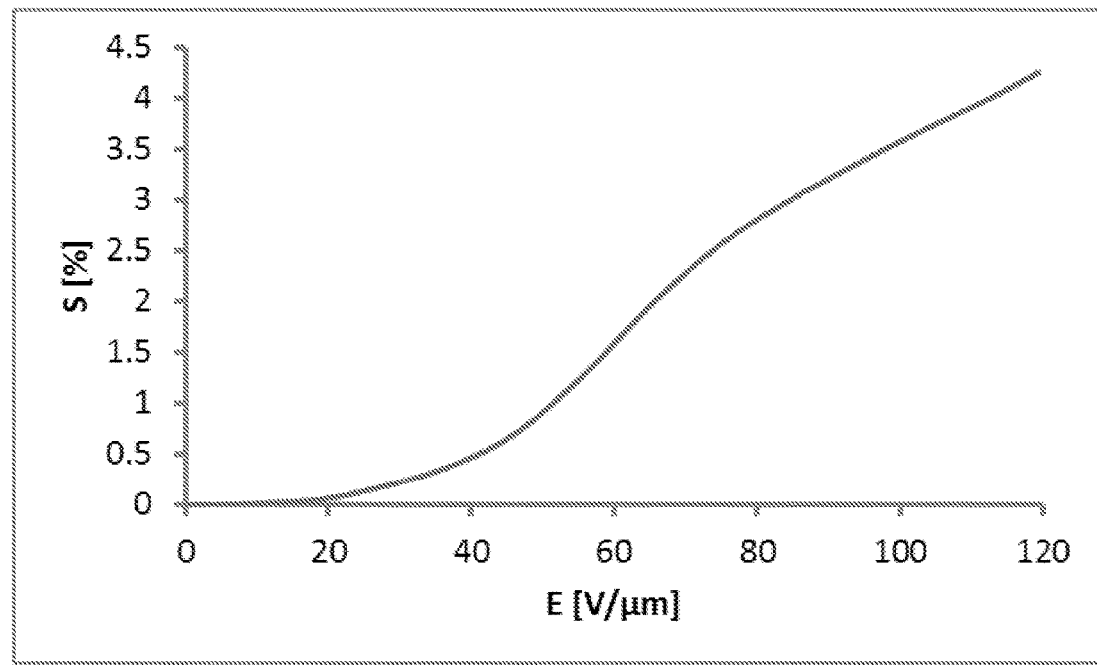
FIG. 3 shows a strain-voltage curve for a typical EAP suitable for use within the invention.

FIG. 3 shows an exemplar strain-voltage curve for a typical electro-active polymer, with the strain corresponding to total incurred deformation as a proportion of the total length of the material, and E corresponding to the electric field applied across the material. Unlike the strain-temperature relationship for SMAs (illustrated in FIG. 2), there is, for electro-active polymers, a one-to-one relation between the two, such that a zero voltage always returns the material to a single particular zero-strain (undeformed) shape.

The particular EAP to which the curve of FIG. 3 corresponds is a field driven relaxor ferroelectric EAP. The strain versus applied electric field relation shown is typical for PVDF based terpolymer systems, such as PVDF-TrFE-CFE. The PVDF-TrFE-CFE material typically has a relatively high elastic modulus compared to other EAPs such as ionic polymers and dielectric elastomers and is therefore able to deliver significant forces on activation.

It should be understood however that embodiments of the invention are by no way limited to these particular example EAP materials, and any variety of EAP may alternatively be considered.

Figure 4:
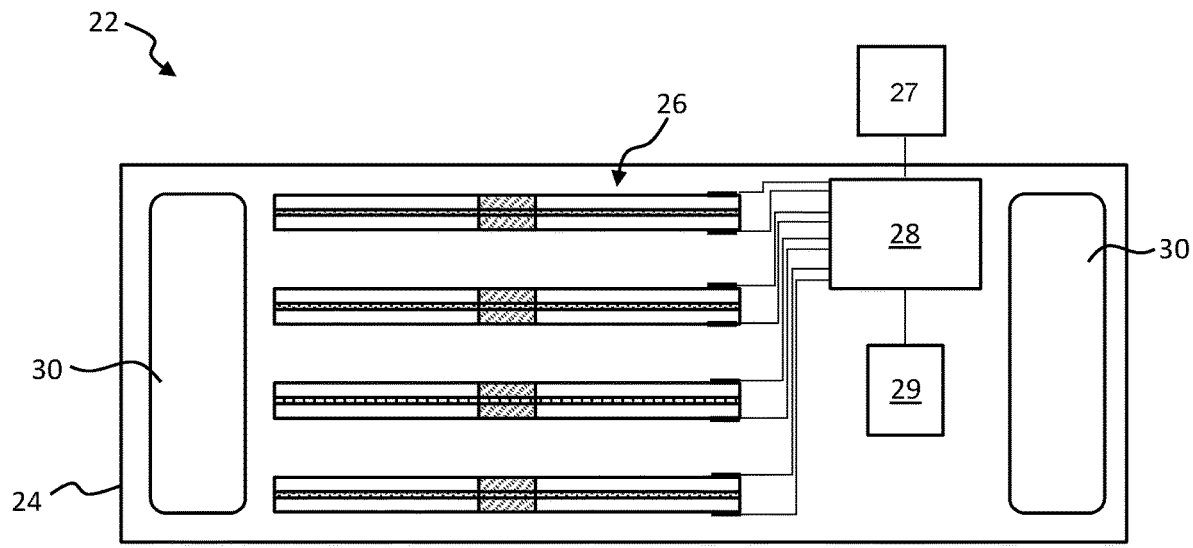
FIG. 4 shows an example device is accordance with an embodiment of the invention.

In FIG. 4 is shown a first example of a health device 22 in accordance with an embodiment of the invention. The device comprises a thin flexible strip or patch 24 to which is coupled or incorporated a plurality of actuator members 26, arranged in a column running across the width of the device 22. Each of the actuator members is electrically connected to a controller unit 28, also coupled to the surface of the flexible strip. The controller is powered by a battery unit 29 also provided coupled to the strip. The strip further comprises an adhesive patches 30 disposed at both ends for securing the strip to a user's skin while the device is in use.

Figure 5:
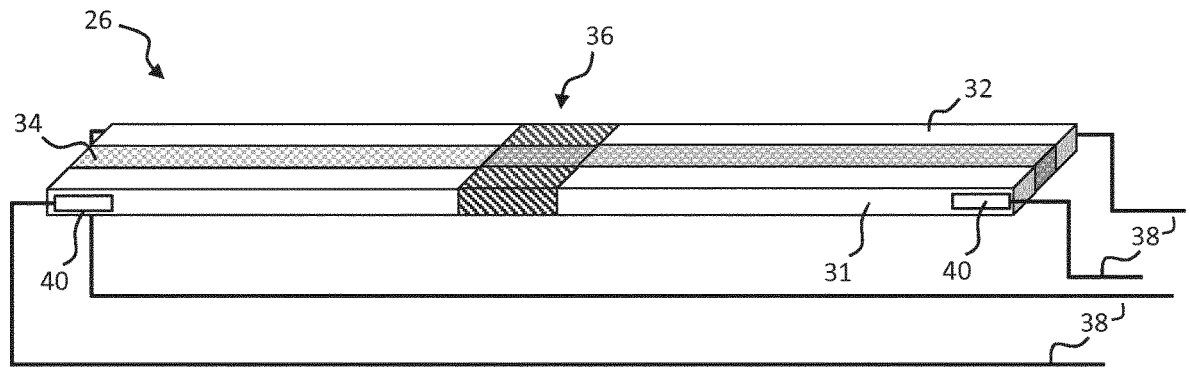
FIG. 5 shows a first example actuator member as may be comprised by embodiments of the invention.

In the particular example of FIG. 4, the actuator members 26 comprise layers or strips of shape memory alloy material. Note that the term layer does not imply any particular stacking, and indeed the layers are side by side in this example. A perspective view of an example actuator member is shown in FIG. 5. Each member 26 comprises a first 31 and second 32 layer of SMA, the layers being separated by a thermal insulating layer 34 adapted to thermally isolate the two SMA layers, such that they may be stimulated and deformed independently of one another. At the centre of the actuator member is a pressure application region 36 which, when the actuator is activated, is pushed upward (out of the page with respect to FIG. 4), hence applying—when the device is inverted and applied to the skin of a user for use—a downward pressure on the point of the user's skin disposed below the pressure application region 36.

Note that in the example shown, the pressure application region 36 constitutes merely a particular area or region of the material layers forming the actuator member 26 (i.e. each of SMA strips 31 and 32 run continuously from the left-most side of the member to the right-most side, and the pressure application region is simply a central portion of these continuous strips.

However, in alternative examples, the pressure application region may comprise a separate element, being composed of a distinct material to the surrounding layers. In some examples, this may be an SMA material of a different composition to that of one or both of the SMA layers 31, 32. Alternatively, it may comprise a conductive non-SMA material, such that current may still pass freely between each of the halves of each SMA layer 31, 32. In further examples still, it may be formed of a non-conductive material. In this case, dedicated connection strips may be provided to electrically connect the two halves of each SMA layer element 31, 32 with one another, or alternatively to electrically connect the left-side halves together and the right-side halves together. In the latter case, the actuator member would be operated by actuating left and right sides as separate, thermally isolated layer elements, rather than the front 31 and back 32 strips.

Referring again to the example of FIG. 5, each of the two SMA layers 31, 32 is provided with a separate pair of electrical connections 38 to the controller 28, for delivery of electrical current across the layer, via electrode members 40. The application of electrical current to either one of the two layers stimulates Joule heating of the layer, hence increasing the temperature of the material. As the temperature rises from below to above the phase transition temperature of the SMA material, the material layer is stimulated to deform into its memory shape.

As described above, the shape-change of shape-memory alloy materials is not inherently reversible: an additional external force is required to 'reset' an SMA back to its original shape once it has deformed and cooled to below its phase-transition temperature. By providing two separate layers of SMA material, mechanically coupled to one another, but thermally isolated, it is possible to achieve this bi-directionality simply by ensuring that the two layers are provided having differing shape-memory shapes. In particular, the first layer is provided having a shape-memory shape which corresponds to an 'actuation' state, and the second layer is provided having a shape-memory shape which corresponds to an idle or flat state.

By heating the first layer 31 (while leaving the second 32 unheated), the actuator member 26 is induced to deform into a bent, actuated state, with the stress released by the phase change of the first layer sufficient to bend both the insulating layer and the second layer (still in its malleable martensite phase) into the same deformed shape-change shape of the first layer 31. By heating the second layer 32 (once the first layer has one again cooled to its malleable martensite phase), the actuator member is, by similar principles, induced to re-deform back into its flat, idle shape.

Figure 6A:
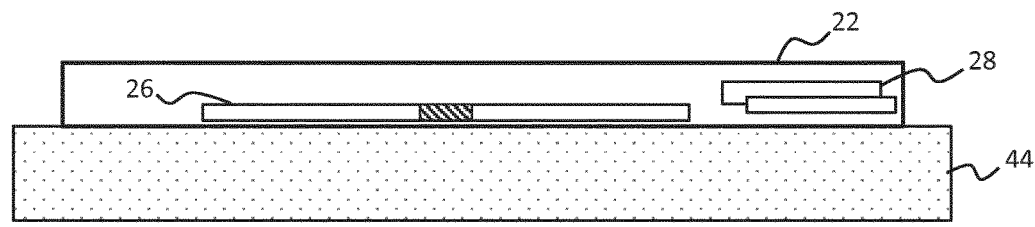
FIGS. 6a and 6b illustrate the un-actuated and actuated states respectively of an example device in accordance with an embodiment.
Figure 6B:
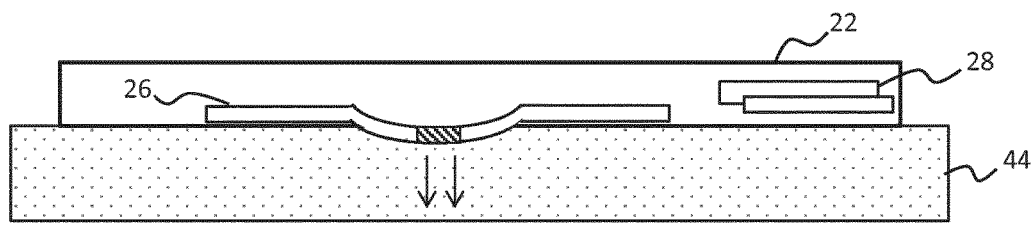

FIGS. 6a and 6b depict a side view of the example health device 22 of FIG. 4, shown in situ, with the actuator members 26 pressed against the surface of a region of a user's skin 44. FIG. 6a shows the device during a flat, idle state, and FIG. 6b shows the device in an active, actuated state, where the first SMA layer 31 has been stimulated to deform into its shape-change shape.

By alternately heating the first 31 and second 32 layers (ensuring to allow the other to cool in the interim), pressure may be alternately applied (FIG. 6b) or released (FIG. 6a) to the regions of the user's skin disposed below the pressure application regions 36 of the actuator members 26. This alternate stimulation is controlled by the controller unit 28 which is configured to apply electrical stimulation (for Joule heating) to the SMA layers of the actuator member in accordance with one or more pre-determined patterns, programs or regimes. These patterns may correspond to particular pressure-application sequences employed by professionals in the administering of particular acupressure therapies. In particular, the controller 28 may be configured to control the stimulation of the first 31 and second 32 layers so as to generate from the device a pressure-application pattern which exactly replicates the pattern applied in the administering of acupressure therapy for insomnia.

According to certain examples, the controller 28 may be configurable to operate in a plurality of different modes, where each mode corresponds to a different particular pattern or program of pressure application. These differing patterns may correspond for example to acupressure therapies suitable for the treatment of different particular conditions or ailments. Alternatively some or all of the patterns may correspond to differing levels or intensities of treatment for one or more of the same ailments or conditions.

The device 22 may in examples comprise one or more user interaction elements adapted to receive user input commands for transmission to the controller unit 28. The controller may be adapted for example to change between one or more modes of operation in response to certain dedicated user input commands.

Note that in some embodiments, especially where high frequency actuation is desired, dedicated cooling elements may be provided to allow more rapid reduction of the temperature of layer elements 31, 32 back to below their phase transition temperatures. Alternatively, one or more heat sink or heat dissipation elements may be provided in thermal communication with one or both of the layer elements to aid in the dissipation of heat from theses layers. However, in other embodiments, such provision may be unnecessary—in particular, where the transition from actuation state to idle state is not required to be achieved at high speed.

In examples, the thermal insulating layer 34 may comprise a flexible thermal barrier material, such as rubber or a rubber-ceramic composite, open or closed cell foam or fabric.

Although in the particular example of FIG. 4, the device 22 is shown as comprising an adhesive patch 32 for securing the device to the skin of the user while in use, in alternative embodiments, other securing means may be provided. These might include, by way of non-limiting example, a clasp or catch, wherein the device comprises a band or strip adapted to curve or fold around a particular region of a user's body (e.g. the wrist or neck), with two ends of the device then held together by means of said clasp or catch, securing the strap in place. Such means might be provided in place of, or in combination with adhesive patches or elements. Alternatively or additionally, the device may, according to one or more examples, be formed as a closed, elasticated loop, such that elastic tension of the loop may be used to hold the device secured around a region of the user's body.

According to one or more particular examples, the embodiment of FIG. 4 may be further configured to provide the additional functionality of sensing and identifying the locations of Acupoints (or Bioactive points) on a user's skin. As discussed in preceding sections, Bioactive points are characterised anatomically in being locations having a high density of nerve fibre bundles, which in turn causes the skin in the vicinity of these points to exhibit a very low electrical resistance. The locations of these points on the skin may therefore be identified, through locating areas or points on the skin where impedance is low compared to surrounding areas.

This may be achieved by means of the device 22 of FIG. 4, through using one or both of the SMA layers 31, 32 to apply low-amplitude electrical signals to the skin of a user, and monitoring parameters of the applied signal (by means of the controller) in order to obtain measurements of skin impedance. For example, the controller 28 may be configured to monitor the voltage and current of the applied signal in order to determine an impedance across the skin.

The required current for such measurements is very low—too low to cause actuation of the actuator member. Joule heating typically requires high currents. For example a 1×1 mm$^2$ square cross section wire of 10 cm long requires approximately 5 A of current to be applied for a duration of 2 seconds to increase in temperature by 20°. For such a wire 0.4V would yield a 5 A current. By contrast, impedance of the skin is typically in the order of 10 kΩ to several hundred kΩ and current at 1V would be <<1 mA.

To achieve effective sensing, it is necessary to ensure that the majority of any provided sensing current be directed through the (high impedance) skin, rather than allowed to pass through the (much lower impedance) SMA layers themselves. To achieve this, a different distribution of applied voltages (across the four electrode members 40) is necessary for sensing than for actuation.

Figure 7:
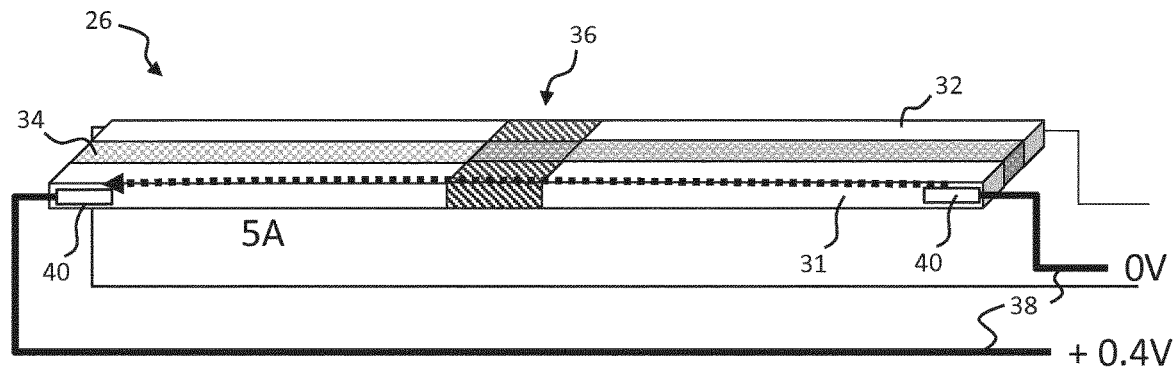
FIG. 7 shows an example electrical configuration of the first example actuator member, for operating the member in an actuating mode.
Figure 8:
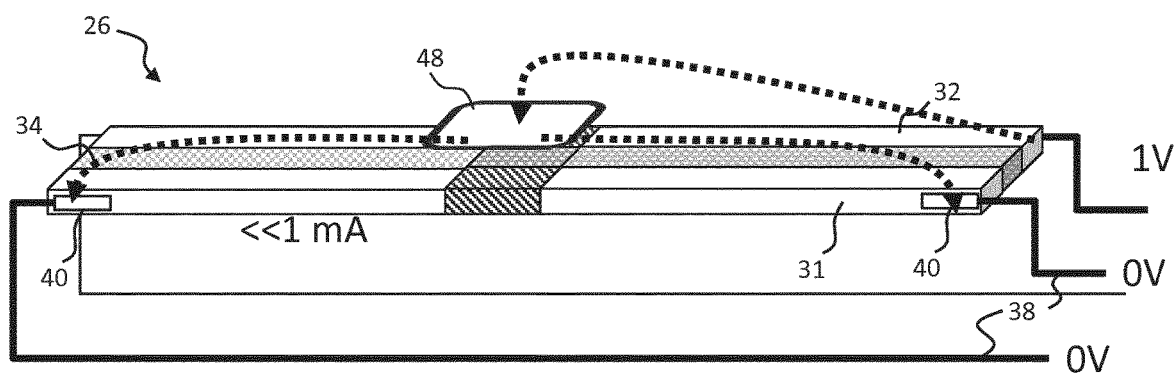
FIG. 8 shows an example electrical configuration of the first example actuator member, for operating the member in a sensing mode.

This is demonstrated in FIGS. 7 and 8, in which electrically active electrode members 40 are indicated by bold electrical connections 38 and electrically inactive electrode members are indicated by fine electrical connections. FIG. 7 illustrates an example electrical configuration for stimulating actuation (of first SMA layer 31 only). Here, a potential difference (of 0.4V) is applied across the electrode members 40 of a single given SMA layer, thereby inducing a current to pass through the SMA material, stimulating Joule heating and deformation.

FIG. 8 shows the contrasting configuration for facilitating sensing. Here, a potential difference of 1V is applied, not between electrode members of any single given SMA layer, but rather between electrode members of different SMA layers. In particular, both electrodes of the first SMA layer 31 are grounded, and one of the electrode members of the second SMA layer is supplied with a positive voltage. The isolation layer 34 is provided being both thermally and electrically insulating, hence forcing electrical connection between the electrodes of the differing layers to be made via the skin (illustrated by skin region 48), and thus inducing a flow of current across the skin.

The controller 28 may be configured to monitor the impedance continuously or periodically as a user moves the device 22 over a broader region of their skin, and to determine thereby when a point of minimum impedance has been reached—indicating the presence of an acupoint.

At this point, one or more user interaction elements 27, for example one or more sensory output elements, may be activated to alert the user that an acupoint has been identified and that the device should be held still at its present location.

By way of example, the controller 28 may comprise a memory and be configured to store each measured value of impedance as the device is moved across the user's skin. In this way, a point of minimum impedance may be determined by simply comparing each new measured value with the stored values in the memory.

A user may be required for example to perform at least one initial 'sweep' across a region of skin in order to obtain an initial set of impedance readings, and then move the device back over the same region, such that the device may then indicate to them at which point a local impedance minimum was found during the first sweep.

Alternatively, minima detection may be performed dynamically, without the need for acquiring an initial set of values, through simply calculating differences and/or rates of change in differences between subsequent impedance values as a user moves the device over a region of their skin. In this way, a minimum may be identified by, for example, identifying a point at which impedance measurements suddenly switch from decreasing in value to increasing in value.

The sensory output elements might include for example one or more acoustic output elements (e.g. speaker elements) or one or more light emitting elements (e.g. LEDs or filament bulbs). The sensory output elements might include one or more haptic output elements for providing a vibration-based signal to a user for example.

In other alternative examples, identification of acupoints may be achieved through the comparison of measured impedance values with one or more pre-determined or pre-stored reference values. These reference values might be for example reference threshold values against which measured values are compared to determine whether they exceed or meet the thresholds, with meeting or exceeding one or more of the thresholds triggering the issuance of an alert to the user.

Note that for the particular example described above, impedance measurements are acquired through electrical stimulation which is applied to the user from across the entire length of one or both SMA layers 31, 32. In alternative examples, the device 22 of FIG. 4 may be adapted such that only one or more limited portions or regions of the SMA layer(s) are utilised in applying stimulation to the skin and in obtaining impedance measurements.

In one example, the application of sensing currents may be achieved through the use of a separate dedicated electrode element, provided for example to the skin-contacting portion of the pressure application zone 36. This electrode element may be provided a dedicated electrical connection with the controller unit 28. In this way, sensing functionality may be provided completely independently of actuation functionality. The two may, if desired, be performed simultaneously for instance.

In another example, the conductive alloy of the SMA layer(s) 31, 32 may still be used to deliver the electrical stimulation to the skin, but the larger area may be adapted such that only one small portion or region of the layer is used in delivering this stimulation. For example the 'upper' (skin-contacting) surfaces of the SMA layers (as depicted in FIG. 4) may be provided with electrically insulating coatings which leave only one or more small portions of the surfaces exposed. In this way, on application of the device to a user's skin, only the exposed portions deliver stimulation to a user.

The advantage of limiting the area over which stimulation is applied is that impedance measurement may be obtained which are more spatially localised, allowing for more precision in pinpointing the specific location of acupoints.

One advantage of utilising the SMA layers 31, 32 themselves for both actuation and sensing is that fewer electrical components and control elements need to be provided, and in addition, it allows that the area over which impedance is measured at any given time corresponds exactly to the region where actuation may subsequently be applied, if it is determined that said region corresponds to an acupoint.

The example actuator member shown in FIG. 5 represents just one of a range of possible configurations for this component.

Figure 9:
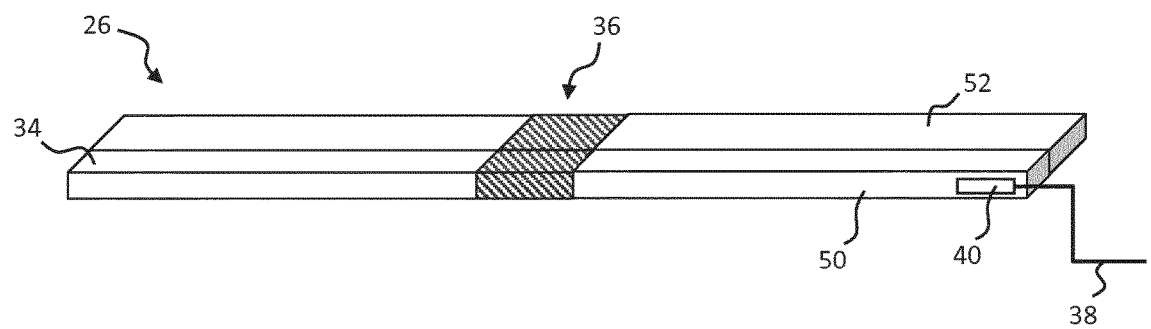
FIG. 9 shows a second example actuator member as may be comprised by embodiments of the invention.

FIG. 9 depicts a second example arrangement for an actuator member in accordance with embodiments of the invention. In this example, just as in the example of FIG. 5, the actuator member comprises two layers 50, 52 of shape memory alloy material. The layers according to this example, however, are not thermally isolated from one another (there is no thermal insulation layer provided), with the first layer 50 being coupled directly to the second 52.

The second layer 52 is provided having a phase transition temperature, T2, which is higher than the phase transition temperature, T1, of the first 50. The two layers may in examples be comprised of the same shape memory alloy material or different shape memory alloy materials. In addition, the second layer is provided having a thickness which is slightly greater than the first. A single electrical connection 38 is provided between the actuator member 26 and the controller 28, for delivering, via electrode element 40, a current across all layers of the actuator arrangement.

The bi-directionality of the actuator member 26 is achieved though the same principle as in previously described example of FIG. 5—with the deformation of the first layer element 50 configured to provide the forward actuation force, and the deformation of the second layer element 52 configured to provide a reversing force to reset the actuator member 26 back to its flat, idle state. Since the two layers are provided having differing phase transition temperatures—the second layer 52 having a higher transition temperature than the first 50—both may be heated simultaneously as a single thermal system, with an initial increase in temperature from below to above T1 (but below T2) triggering deformation of the first layer 50—and hence actuation—and a subsequent increase from below to above T2 triggering deformation of the second layer 52 and hence resetting of the actuator member 26.

On increase from below to above T2—for triggering resetting of the actuator—the first layer element 50 remains throughout in its high-temperature austenite phase, and hence in a high modulus of elasticity, low-flexibility state. However, since the second layer element 52 is provided with a slightly greater thickness than the first, the force brought up by its phase transition and shape change is sufficient to exceed the resistive forces of the first layer element, and return the actuator to its flat configuration. As the temperature is then once again lowered back to below T1, the shape of the actuator member does not change, and the device remains in its reset state.

In general, in order for the second layer 52 to overcome the resistive force of the first layer 50 during its transition back to the idle, flat state, and so induce the entire actuator member 26 to adopt this shape, the force delivered by the second layer 52 in its high temperature phase must exceed that delivered by the first layer 50 when in its high temperature phase. Where the layers are constituted of the same material, or, more broadly, where the high temperature elastic moduli of the two layers are very similar, the above requirement is met if the second layer 52 has a thickness which is greater than that of the first layer 50 as explained above. This derives from the fact that (permitting reasonable simplification), in general, the force exerted (per unit length) by a layer of material of thickness d and Elastic modulus E can be broadly approximated by E*d. Therefore, for materials of very similar E, and in particular for layers of the same length, the force exerted by one will exceed that exerted by the other, only if the thickness of the first is greater than the second.

However, in an alternative example, elastic moduli of the two layers 50, 52 differ from one another—in one or both phases of the materials. In this case, the condition that the force of the second layer 52 exceed that of the first 50 when both are in their high temperature phases is met by the broader approximated condition that E*d of the second layer exceed that of the first when at the relevant high temperature.

Thus, the two layers 50, 52 may be comprised of the same shape memory material, or may constitute different materials, but in either case, the two possess differing phase change temperatures.

The whole bi-layer structure moves as a single, cohesive body, with each layer mechanically co-dependent with the other. The two layers are thus connected together with strong connections, preferably over the total surface without air gaps, but such that each retains its specific material properties.

According to both of the above particular example actuator member configurations, the provided actuator member 26 (see FIGS. 5 and 9) is thermally stimulated through the direct application of an electrical current to the material layers and the consequent Joule heating of the SMA material.

Figure 10:
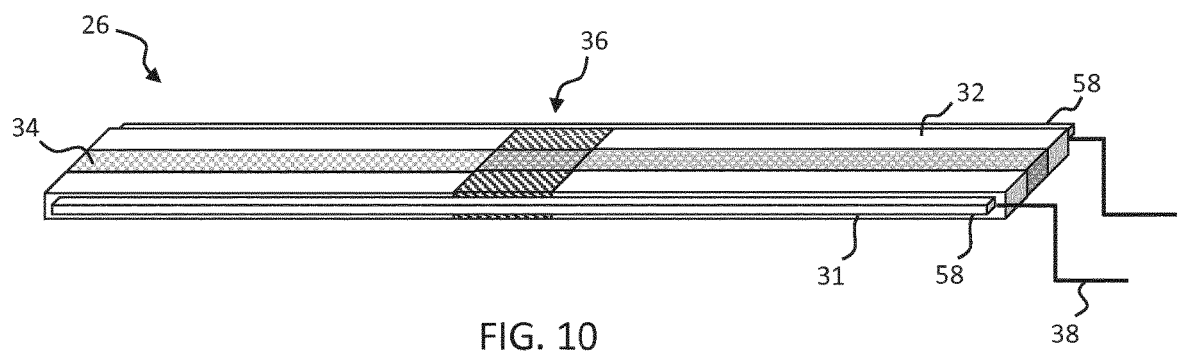
FIG. 10 shows a third example actuator member as may be comprised by embodiments of the invention.

In an alternative set of examples, however, thermal stimulation of the SMA layers is achieved through the provision of one or more dedicated heater elements, thermally coupled with the layer elements. An example of such a configuration is illustrated in FIG. 10 which depicts an actuator member having two (in this case thermally isolated) SMA material layers 31, 32, each provided with a respective heater element 58 thermally coupled to one side of the layer. Each heater element 58 is individually connected to the controller 28 and may be independently activated or deactivated to stimulate heating or allow cooling of the respective layers.

According to a further set of example embodiments, the actuator members may be composed of one or more layers of electroactive polymer material. As discussed above, electroactive polymers change shape in response to the application of an electric field across the material, where the extent of deformation may be controlled by varying the applied voltage. In contrast to shape-memory alloy materials, the deformation of an EAP is directly reversible: a material will remain deformed only so long as an electrical stimulus is applied, and will revert immediately to its original shape as soon as the applied field is removed. Actuator members utilizing EAP materials may therefore be provided comprising only a single layer of the material, as opposed to the bi-layer structures of the SMA example embodiments—since a second layer for 'resetting' is not required.

Figure 11:
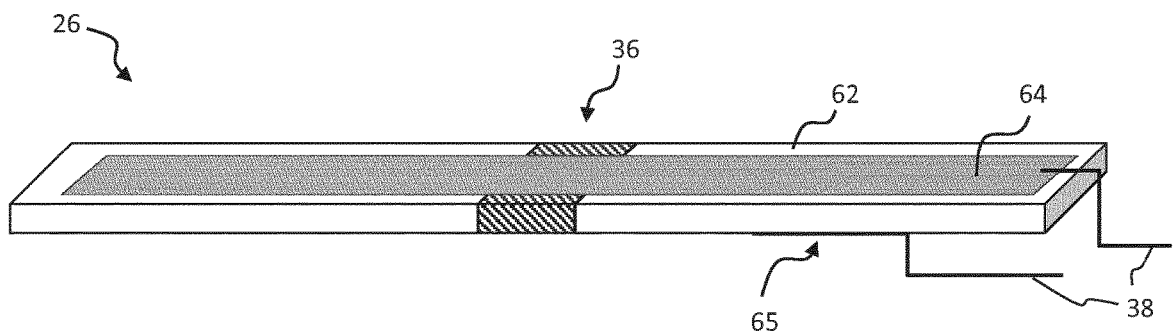
FIG. 11 shows a fourth example actuator member as may be comprised by embodiments of the invention.

An example of an actuator member comprising an EAP material layer is illustrated in FIG. 11. The actuator member 26 comprises a single layer of EAP material 62, having a first electrode member 64 coupled to its upper surface and second electrode member 65 coupled to its lower surface, for application of an electric field across the layer via electrical connection 38 (connected to the controller unit 28).

On application of electrical signals to the electrode members 64, 65, an electric field is established across the EAP layer 62 which stimulates the layer to deform into an 'upward' bend, with the extent of deformation related to the magnitude of the applied field. Note that for some EAPs an additional passive carrier layer is required to create an upward bend. When the actuator member is inverted and applied to the skin of a user, the deformation applies a downward pressure onto a point of the user's skin lying below the pressure application zone 36. On termination of the electrical signal at the electrode member 64, the actuator member returns to the flat configuration depicted in FIG. 11, and pressure is released from the skin of the user.

As in the SMA-based examples described above, embodiments of a health device 22 incorporating the example actuator member 26 of FIG. 11 may be further configured to provide the additional functionality of detecting or identifying locations of acupoints on the user's skin. This may be achieved in the same manner as in these examples—through the application of low level electrical stimulation to the user's skin to obtain impedance measurements, and the subsequent identification of regions or points of local impedance minimum. In the present case, the low-level electrical signals are applied to the skin, not through the material of the actuator member itself (which is not conductive), but instead via an electrode or other conductive element which is arranged to make contact with the user's skin when the device is in use.

In one set of examples, the electrical stimulation is administered through the electrode member 64. Since the member is coupled to the upper surface of the actuator member 26, on inversion of the device (as shown in FIG. 4) for application on the skin, the electrode member 64 is held pressed in contact with the user's skin, allowing for electrical signals to be transferred. In this case, an additional electrode member must be provided somewhere on the upper surface of the actuator member, in order that a circuit may be established across the skin.

Note that when the device is operating in actuation, rather than sensing, mode, the live pole of the high amplitude signal is provided to the second electrode member 65 at the bottom of the EAP (i.e. not on the skin contacting side). The skin contacting electrode will always be in the low state. In this way, it is ensured that the high amplitude signal for actuation is never applied to the skin of the user. In addition, safety may be further ensured by also contacting the 'minus' pole of the power source (in case of a battery) or ground (in case of wall socket connection) to the skin so that the skin is always protected from the high amplitude live electrode and will always be in ground/low state.

Analogously with the SMA example described previously, certain portions or regions of the electrode member 64 may be provided with an electrically insulating covering, to leave only certain sections exposed for application to the user's skin. This would limit the total area over which impedance measures are being taken, and hence provide more localised measurements, allowing for more precise determination of acupoint locations.

According to an alternative set of examples, a separate, dedicated electrode element may be provided coupled to an upper surface of the actuator member 26 for delivery of the electrical stimulation to the user's skin. In this case, the dedicated element is provided a separated electrical connection to the controller 28, to allow operation of sensing functionality independently of actuation functionality.

In accordance with any of the particular embodiments described above, the health device may in examples further comprise one or more additional stimulation elements. For example, the device may comprise a TENS element, for delivery, in addition to the pressure therapy provided by the actuator member(s), of electro-stimulation based therapy. Additionally or alternatively the device may comprise one or more heating elements for delivering low-level heat-based therapy to the user. These might in examples include one or more infrared LED elements for instance.

In one or more examples, the device might additionally incorporate one or more temperature sensors and/or humidity sensors. Audio output components may be provided for playing music and/or sound recordings, for example to aid in the relaxation of a user.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A health device for applying pressure to one or more areas of a user's skin, comprising:
   one or more actuator members, each comprising a smart shape-changing material of a class which is disposed to change shape in response to a change in temperature or to the application of an electrical stimulus;
   one or more stimulating means to deliver first electrical or thermal stimuli to the one or more actuator members for stimulating shape change of the smart shape-changing material, the one or more stimulating means comprising electrodes, electrically coupled to the smart shape-changing material of each of the one or more actuator members; and
   a controller operatively coupled with, and adapted to control the one or more stimulating means to deliver the first electrical or thermal stimuli to the shape-changing material in order to stimulate the smart shape-changing materials of the one or more actuator members to deliver pressures to one or more pressure delivery areas of a user's skin,
   wherein the device comprises one or more skin stimulation elements, electrically connected with the controller, for transferring second electrical stimuli generated by the controller to one or more areas of a user's skin, wherein the second electrical stimuli are for sensing an impedance of the skin, and wherein the controller is adapted to determine the impedance of the skin through measuring one or more electrical parameters of the delivered second electrical stimuli.

2. A health device as claimed in claim 1, wherein the controller is adapted to control the one or more stimulating means such that the shape-changing materials of the actuator members are stimulated to deliver pressures which vary in magnitude over time, so as to enable administration by the device of an acupressure therapy.

3. A health device as claimed in claim 1,
   wherein the health device is a wearable health device comprising a securing means for holding the one or more actuator members against the one or more pressure delivery areas of a user's skin.

4. A health device as claimed in claim 1,
   wherein the smart shape-changing material is a shape memory alloy material, disposed to change between a first shape and a second shape in response to a change in temperature from below to above a particular phase transition temperature, and wherein the controller is adapted to deliver voltages to the electrodes coupled to the shape memory alloy materials of each actuator member in order to stimulate Joule heating of said shape memory alloy materials.

5. A health device as claimed in claim 4, wherein the one or more skin stimulation elements are formed by one or more area portions of the shape memory alloy materials.

6. A health device as claimed in claim 4, wherein each of the one or more actuator members comprises a first shape memory alloy layer, a second shape memory alloy layer, and a thermal insulating layer disposed between the first and second shape memory alloy layers.

7. A health device as claimed in claim 4, wherein each of the one or more actuator members comprises a first shape memory alloy layer and second shape memory alloy layer, the second being coupled to the first, and wherein the first and second layers have different phase transition temperatures.

8. A health device as claimed in claim 1,
   wherein the smart shape-changing material is an electroactive polymer material disposed to change shape in response to the application of the first electrical or thermal stimuli, and wherein the controller is adapted to deliver voltages to the electrode for electrically stimulating the electroactive polymer material to change shape.

9. A health device as claimed in claim 8, wherein the one or more skin stimulation elements are formed by one or more area portions of the electrodes coupled to the electroactive polymer materials of the actuator elements.

10. A health device as claimed in claim 1, wherein the controller is operable to perform the steps of:

periodically or continually determining an impedance of the skin through measuring one or more electrical parameters of electrical stimuli delivered to the skin of a user by means of the one or more skin stimulation elements, thereby obtaining a set of skin impedance measurements;

analysing said determined impedance of the skin by comparing it with one or more reference values in order to determine whether said value corresponds to a minimum impedance point of the user's skin;

generating a sensory output by means of one or more sensory output elements, one or more parameters of the sensory output being dependent upon the result of said determination of whether or not the determined impedance corresponds to a minimum impedance point.

11. A method of delivering pressure to one or more areas of a user's skin by means of a health device, the health device comprising one or more actuator members' each comprising a smart shape-changing material of a class which is disposed to change shape in response to a change in temperature or to the application of an electrical stimulus, one or more stimulating means to deliver thermal or electrical stimuli to the one or more actuator members, for stimulating shape change of the smart shape-changing material, and one or more skin stimulation elements;

the method comprising:

controlling the one or more stimulating means to stimulate the shape shape-changing materials of the one or more actuator members to deliver pressures to one or more pressure delivery areas of a user's skin; and delivering electrical stimuli to one or more areas of the user's skin through the one or more skin stimulation elements and determining an impedance of the skin by measuring one or more electrical parameters of the delivered electrical stimuli.

* * * * *